United States Patent [19]
Newman et al.

[11] Patent Number: 5,762,071
[45] Date of Patent: Jun. 9, 1998

[54] KIDNEY STONE SPECIMEN COLLECTION SYSTEM

[76] Inventors: Dennis Newman, 3519 Grennoch, Houston, Tex. 77025; Ronald B. Stein, 8810 Weymouth Dr., Houston, Tex. 77031

[21] Appl. No.: 708,375

[22] Filed: Sep. 4, 1996

Related U.S. Application Data

[60] Provisional application No. 60/009,260 Dec. 26, 1995.

[51] Int. Cl.⁶ .................................................. A61B 5/00
[52] U.S. Cl. ................................. 128/760; 604/329
[58] Field of Search .................... 128/760; 604/317, 604/327, 329, 349, 268; 210/645, 459, 477; 209/158

[56] References Cited

U.S. PATENT DOCUMENTS

| | | | |
|---|---|---|---|
| 1,098,653 | 6/1914 | Whisenant. | |
| 1,213,320 | 1/1917 | Whitaker. | |
| 2,628,819 | 2/1953 | Parsons | 210/477 |
| 2,885,084 | 5/1959 | Rocca | 210/464 |
| 2,896,788 | 7/1959 | Hoffberger | 210/473 |
| 3,880,311 | 4/1975 | McPhee | 604/260 |
| 4,040,964 | 8/1977 | Hegyi | 210/238 |
| 4,357,240 | 11/1982 | Metira et al. | 210/455 |
| 4,777,137 | 10/1988 | Lemonnier | 210/477 |
| 5,078,800 | 1/1992 | Cahill | 134/25.3 |
| 5,331,689 | 7/1994 | Hag | 4/144.1 |
| 5,503,742 | 4/1996 | Farley | 2109/459 |

*Primary Examiner*—Robert A. Clarke
*Attorney, Agent, or Firm*—Harrison & Egbert

[57] ABSTRACT

A kidney stone specimen collection device having a tubular body with a longitudinal axis, a mesh screen affixed to an interior of the tubular body and extending transverse to a longitudinal axis of the tubular body, a first closure member affixed to one end of the tubular body so as to selectively seal the end of the tubular body, and a second closure member affixed to an opposite end of the tubular body for selectively sealing the opposite end of the tubular body. The tubular body is formed of an impact-resistant generally transparent plastic material. A flow indicator is positioned on a surface of the tubular body so as to be indicative of a direction of urine flow through the tubular body.

19 Claims, 1 Drawing Sheet

KIDNEY STONE SPECIMEN COLLECTION SYSTEM

RELATED APPLICATIONS

The present application is a utility patent application which is based on U.S. Provisional patent application Ser. No. 60/009,260, filed on Dec. 26, 1995, and entitled "KIDNEY STONE SPECIMEN COLLECTION SYSTEM", presently pending.

TECHNICAL FIELD

The present invention relates to devices for the collection of kidney stones from a urine stream. More particularly, the present invention relates to containers for the receipt and capture of kidney stones.

BACKGROUND ART

It is a well known fact, at least to those of the medical profession, that there are hundreds of thousands of people in this country chronically or critically suffering from kidney stone afflictions. The patient is often advised to retrieve the foreign particles for purposes of clinical examination. This presents an obvious problem of inconvenience and perhaps embarrassment, particularly when it is impossible to have ordinary suitable household utensils at hand for the required purpose.

Under conventional circumstances, the person afflicted with kidney stones is required to urinate through a funnel-like strainer. Whenever a kidney stone passes, it will be captured by a screen within the strainer. After the kidney stone is separated from the urine stream, the patient is required to remove the kidney stone from the strainer and capture it in a bottle or other container. The kidney stones contained within the bottle are then delivered to a physician or a clinic for analysis. In any event, these procedures are often difficult, cumbersome, unsanitary, and inconvenient. Fingers or tweezers must often be used so as to transfer the specimens from the funnel to the specimen bottle.

In normal use, the conventional system cannot be conveniently carried with the patient to be used outside the home due to the size and shape of the conventional system. It is often not used because of the difficulty of use and because of privacy requirements. Thus, the patient is not likely to use the existing system outside of the home. This results in the loss of specimens emitted when the collection system is not used in places outside of the home. The system makes loss of specimens likely due to the need to transfer specimens from the collection funnel to the specimen bottle when it is used. This system potentially causes contamination of specimens if the patient handles, drops, or otherwise exposes the specimen during the transfer from funnel to bottle. The system can be unsanitary in that the patient frequently will handle both the exposed screen in the funnel and the specimen itself.

In the past, various U.S. patents have issued relating to devices for the collection of kidney stones. For example, U.S. Pat. No. 2,896,788, issued on Jul. 28, 1959, to C. C. Hoffberger describes a foldable strainer device. The foldable strainer device is made of a cardboard or paperboard material. The strainer device has a configuration of a inverted truncated pyramid. A screen or strainer is positioned on the interior of the device. In normal use, the patient will urinate in one side of the strainer device, through the screen, and out the opposite end of the device. When the device is not in use, it can be folded into a convenient arrangement. Once again, as with the existing prior art, the device requires that the patient remove the kidney stone specimen from the interior of the strainer device so as to transfer the specimen into a bottle. Additionally, the use of cardboard material can cause the device to deteriorate quickly and be in an unsanitary condition.

U.S. Pat. No. 5,331,689, issued on Jul. 26, 1994, to A. Haq teaches a portable urinal apparatus including a urine-receiving member having an inlet and an outlet. The inlet is sized and shaped for receiving a flow of urine from an individual using the apparatus. A screen is disposed between the urine-receiving member and the conduit for catching and retaining foreign material in the flow of urine from the urine-receiving member. This device is a fairly complicated apparatus that is designed for use in a hospital environment.

It is unlikely that one would be able to conveniently use such a portable urinal out of a confined environment. This device does not provide an easy method for the collection of kidney stone specimens.

Various U.S. patents have issued in the past which have described various types of bottles for the collection of U.S. Pat. No. 1,098,653, issued on Jun. 2, 1914, to M. B. Whisenant teaches a bottle having a screen formed on the interior of the bottle. U.S. Pat. No. 1,213,320, issued on Jan. 23, 1917, to S. T. Whitaker teaches a sanitary drinking apparatus in which a screen is fitted into the mouthpiece of the apparatus. The screen extends between one open end and another open end. U.S. Pat. No. 2,885,084, issued on May 5, 1959, to J. Rocca has a screen filter that is useful on milk containers. U.S. Pat. No. 4,040,964, issued on Aug. 9, 1977, to E. Hegyi describes an adjustable container strainer and handle in which a tubular member is provided with a screen located on the interior of the tubular member. The device can be used for straining fluids from materials on the interior of the tubular member. U.S. Pat. No. 4,357,240, issued on Nov. 2, 1982, to Mehra et al. describes a disposable filtration unit wherein the body of the unit is a unitary, one-piece molded structure having an internal flange for dividing the unit into upper and lower chambers. U.S. Pat. No. 5,078,800, issued on Jan. 7, 1992, to J. A. Cahill describes a treatment container for washing and rinsing materials. This container includes a body with an open top and a screen or mesh in proximity to the top of the body for allowing drainage of excess cleansing fluid and washed-off substances during cleansing of the material while retaining the material within the interior of the container.

It is an object of the present invention to provide a system for the collection of kidney stones that can effectively collect kidney stones from a urine stream.

It is another object of the present invention to provide a system which is transportable and easy to use.

It is a further object of the present invention to provide a system in which the container can be closed and sealed without the need for transferring the kidney stone to a separate container.

It is a further object of the present invention to provide a system which avoids contamination of the kidney stone specimen.

It is still another object of the present invention to provide a kidney stone collection system which is easy to manufacture and relatively inexpensive.

It is a further object of the present invention to provide a kidney stone collection system that can be utilized in pneumatic tube delivery systems.

These and other objects and advantages of the present invention will become apparent from a reading of the attached specification.

SUMMARY OF THE INVENTION

The present invention is a kidney stone specimen collection system which includes a tubular body having a screen disposed transversely therein, a first closure member at one end of the tubular body and a second closure member at an opposite end of the tubular body. The tubular body provides a flow passageway through which a urine stream can be directed. The urine stream will pass through the transversely disposed screen. When the closure members are removed from the ends of the tubular member, urine stream will pass freely from one end to the opposite end of the tubular body. Any kidney stones that would pass with the urine stream will be collected on a surface of the screen on the interior of the tubular body.

After kidney stones are collected by the screen, the first and second closure members can be attached to the ends of the tubular body so as to properly seal the interior of the tubular body. The tubular body, with the closure members attached, can then be transported to a clinic, physician, or another location for storage and analysis.

In the preferred embodiment of the present invention, the closure members include caps which are threadedly affixed to the ends of the tubular body. Threads are formed on the ends of the tubular body so as to receive internal threads formed on each of the caps. Preferably, the caps will include a sealing member so as to establish a liquid-tight seal with the ends of the tubular body.

Preferably, the tubular body is an impact resistant plastic bottle, approximately two inches in diameter and approximately three inches long. The screen is a fine mesh screen which is molded transversely to the longitudinal axis of the tubular body.

DETAILED DESCRIPTION OF THE INVENTION

Figure 1:
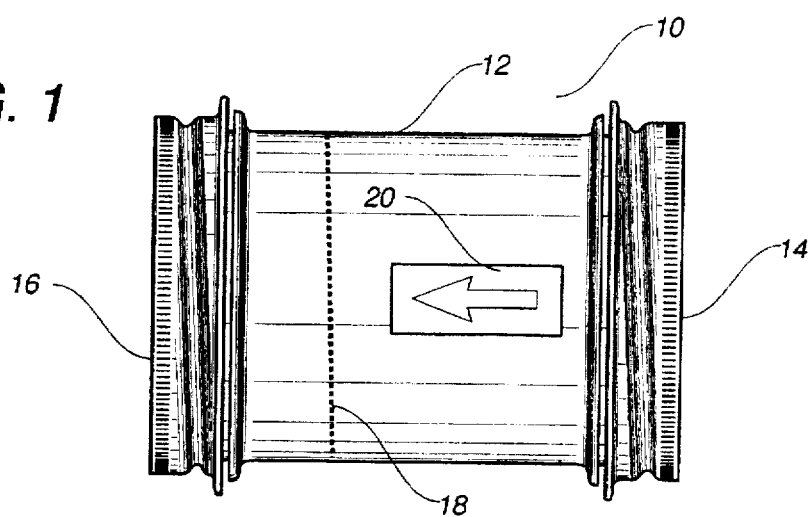
FIG. 1 is a side elevational view of the kidney stone specimen collection system in accordance with the preferred embodiment of the present invention.

Referring to FIG. 1, there is shown at 10 the kidney stone collection system in accordance with the preferred embodiment of the present invention. The kidney stone collection system 10 includes a tubular body 12, a first closure member 14, and a second closure member 16. A screen 18 is disposed transversely to the longitudinal axis of the tubular body 12.

The tubular body 12 is made of an impact-resistant plastic bottle. Ideally, and preferably, the bottle will have a length of approximately three inches and a diameter of approximately two inches. The diameter should not be not less than two inches so as to prevent inadvertent splashing of urine when the system 10 is being used. The tubular body 12 should be relatively transparent so that the user can see the existence of a kidney stone on the screen 18. A flow indicator 20 is positioned on the exterior surface of the tubular body 12. This flow indicator 20 is an indication of the desired direction of urine flow through the interior of the tubular body 12. The indicator 20 can be in the form of a label that is affixed to the exterior surface of the tubular body 12 or it can be an arrow which is molded onto the surface of the tubular body 12. Patient identification information can also be affixed to the surface of the tubular body 12 or to the surfaces of the closure members 14 and 16.

The closure member 14 is affixed to an end 22 of the tubular body 12. Preferably, the closure member 14 is a cap which is threadedly affixed to the end 22 of the tubular body 12. However, in alternative embodiments of the present invention, the closure member 14 can take the form of various other types of closures, such as flip-top caps, flaps, or other items that can effectively close the interior of the tubular body 12. During use, the closure member 14 can be removed so that the flow of the urine stream can pass into the opening at the end 22 of the tubular body 12. The closure member 14 can have a label containing patient information attached thereto. The closure means should have an O-ring elastomeric seal positioned therein. Such a seal can prevent leakage of residual urine from the system 10 when the closure member 14 is placed onto the end 22 of the tubular body 12.

The second closure member 16 is affixed to the opposite end 24 of the tubular body 12. The closure member 16 should have a configuration similar to the closure member 14. As such, the closure member 16 can be a cap which is threadedly affixed to the end 24 of the tubular body 12. During use, the closure members 14 and 16 are removed so as to allow a free flow of urine through the interior of the tubular body 12. When the urine stream is stopped, the closure members 14 and 16 can be affixed to the ends 22 and 24, respectively, of the tubular body 12. This will effectively seal the interior of the tubular body 12 so as to avoid contamination and to avoid any spillage from the interior of the tubular body 12. The second closure member 16 should also have an elastomeric O-ring seal affixed along its inner surfaces. This seal can serve to prevent leakage of residual urine when the closure member 16 is placed on the end 24 of the tubular body 14.

The screen 18 is a fine mesh screen which is affixed to the interior wall of the tubular body 12. The screen 18 extends transverse to the longitudinal axis of the tubular body 12. The edges of the screen 18 extend circumferentially along the interior wall of the tubular body 12. The edges of the screen 18 can be integrally molded with the tubular body 12 so as to assure rigid attachment between the screen 18 and the interior of the tubular body 12. Alternatively, the edges of the screen can be adhesively affixed to the interior wall of the tubular body 12. The screen 18 can also be affixed to the interior wall in an interference fit relationship. The screen 18 can be positioned centrally along the length of the tubular body 12 (as shown in FIG. 1), or it can be positioned adjacent one of the ends 22 or 24 of the tubular body 12. Ideally, the screen 18 should be positioned one-half inch or more from the ends 22 or 24.

Figure 2:
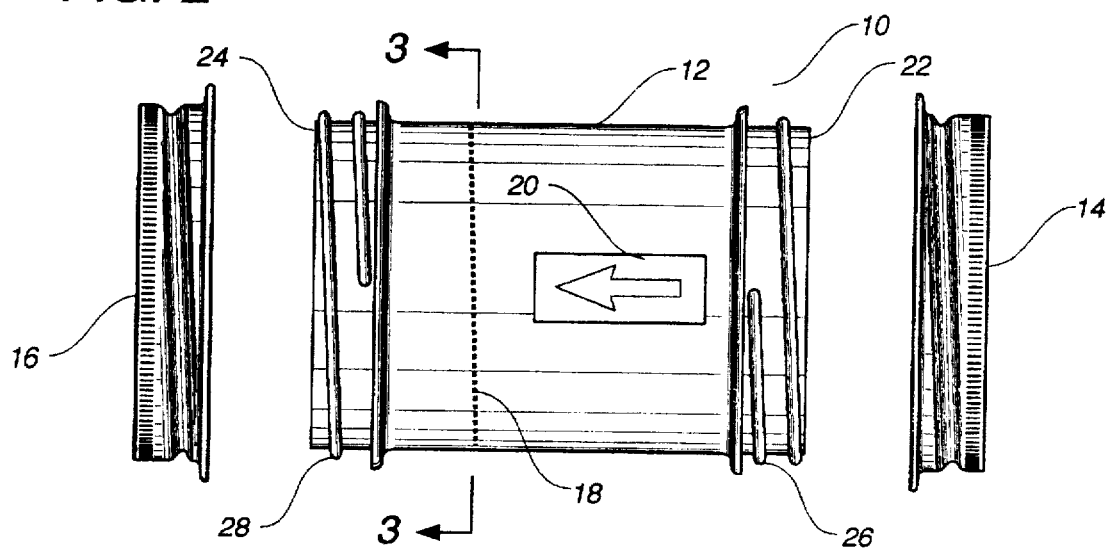
FIG. 2 is an exploded side elevational view of the system of the present invention.

FIG. 2 is an exploded view of the system 10 of the present invention. It can be seen that the tubular body 12 includes an external thread 26 at the end 22 of the tubular body 12 and an external thread 28 at the end 24 of the tubular body 12. These external threads 26 and 28 serve to receive the internal threads the closure members 14 and 16. In alternative embodiments of the present invention, the threads 26 and 28 could be internal threads on the interior of the tubular body 12. Such internal threads could receive external threads on the closure members 14 and 16. Still further, and alternatively, the ends 22 and 24 of the tubular body 12 can include lips that will receive the interior shoulders of flap-like members attached to the ends 22 and 24 of the tubular body 12. Also, press-on sealing lids can be applied to the ends of the tubular body.

Figure 3:
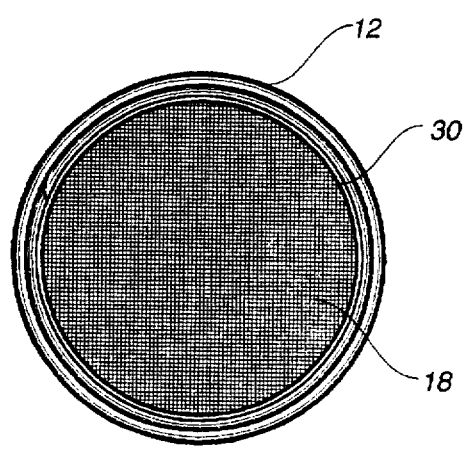
FIG. 3 is a cross-sectional view taken across lines 3—3 of FIG. 2.

FIG. 3 shows the configuration of the screen 18 on the interior 30 of the tubular body 12. It can be seen that the screen 18 is a fine mesh screen that extends entirely across the interior of the tubular body 12. The edges of the screen 18 are molded within the walls of the tubular body 12.

In use, the patient would remove the closure members 14 and 16 from the ends of the tubular body 12. The patient will then urinate into the tubular body 12 in the direction of the indicator arrow 20. Any stone specimens emitted during urination would be trapped on the mesh screen 18. Urine would flow freely through the system into the toilet or urinal. After urination, the patient would screw the caps 14 and 16 on the ends 22 and 24 of the tubular body 12. The process would be repeated by the patient each time he or she urinated during the specimen collection period, as directed by the physician. The bottle will be returned to the physician as directed for specimen analysis. After each use, the system can be carried conveniently in a pocket or purse with no risk of contamination, loss of contents, or embarrassment.

The foregoing disclosure and description of the invention is illustrative and explanatory thereof. Various changes in the details of the illustrated configuration may be made within the scope of the appended claims without departing from the true spirit of the invention. The present invention should only be limited by the following claims and their legal equivalents.

We claim:

1. A kidney stone specimen collection device comprising:
    a tubular body having a longitudinal axis;
    a kidney stone removal means affixed to an interior of said tubular body and extending transverse to said longitudinal axis of said tubular body, said kidney stone removal means for separating a kidney stone from a flow of urine passing through said tubular body, said kidney stone removal means, being a mesh screen, said mesh screen having a porosity suitable for allowing urine to flow freely therethrough;
    a first closure means removably affixed to one end of said tubular body, said first closure means for selectively sealing said one end of said tubular body; and
    a second closure means removably affixed to an opposite end of said tubular body, said second closure, means for selectively sealing said opposite end of said tubular body.

2. The device of claim 1, said tubular body being formed of an impact-resistant plastic material.

3. The device of claim 1, said tubular body having a diameter of no less than two inches.

4. The device of claim 1, said mesh screen being positioned within said tubular body not less than ½ inch from either of said ends.

5. The device of claim 4, said mesh screen positioned generally centrally along said longitudinal axis within said tubular body.

6. The device of claim 1, said mesh screen having an outer edge molded into said tubular body such that said outer edge extends circumferentially around an interior wall of said tubular body.

7. The device of claim 1, said first closure means comprising:
    a cap threadedly affixed to said one end of said tubular body.

8. The device of claim 7, said cap having a sealing means extending circumferentially around an interior of said cap, said sealing means for forming a liquid-tight seal with said tubular body when said cap is affixed to said one end.

9. The device of claim 7, said second closure means comprising:
    a cap threadedly affixed to said opposite end of said tubular body.

10. The device of claim 9, said cap of said second closure means having a sealing means extending circumferentially around an interior of said cap, said sealing means of said second closure means for forming a liquid-tight seal with said tubular body when said cap of said second closure means is affixed to said opposite end.

11. The device of claim 1, further comprising:
    a flow indicator means positioned on a surface of said tubular body, said flow indicator means for indicating a desired direction of urine flow through said tubular body.

12. The device of claim 11, said flow indicator means comprising:
    a label adhesively affixed to an exterior surface of said tubular body, said label having an arrow formed thereon, said arrow being indicative of the desired direction of urine flow.

13. The device of claim 11, said flow indicator means comprising:
    an arrow molded into said tubular body so as to face exterior of said tubular body, said arrow being indicative of the desired direction of urine flow.

14. A kidney stone specimen collection device comprising:
    a tubular body having a longitudinal axis, said tubular body being formed of a generally transparent material;
    a kidney stone removal means affixed to an interior of said tubular body and extending transverse to said longitudinal axis of said tubular body, said kidney stone removal means for separating a kidney stone from a flow of urine passing through said tubular body, said kidney stone removal means being a mesh screen, said mesh screen having an outer edge which contacts an inner wall of said tubular body;
    a first closure means removably affixed to one end of said tubular body, said first closure means for selectively sealing said one end of said tubular body;
    a second closure means removably affixed to an opposite end of said tubular body, said second closure means for selectively sealing said opposite end of said tubular body; and
    a flow indicator means positioned on an exterior surface of said tubular body, said flow indicator means for indicating a desired direction of urine flow through said tubular body.

15. The device of claim 14, said flow indicator means comprising:
    a label adhesively fixed to an exterior surface of said tubular body, said label having an arrow formed thereon, said arrow being indicative of the direction of urine flow.

16. The device of claim 14, said first closure means comprising:
    a cap threadedly affixed to said one end of said tubular body, said cap having a sealing means extending circumferentially around an interior of said cap, said sealing means for forming a liquid-tight seal with said tubular body when said cap is affixed to said one end.

17. The device of claim 16, said second closure means comprising:
    a cap threadedly affixed to said opposite end of said tubular body, said cap of said second closure means having a sealing means extending circumferentially around an interior of said cap of said second closure means, said sealing means of said cap of said second closure means for forming a liquid-tight seal with said tubular body when said cap of said second closure means is affixed to said opposite end.

18. The device of claim 14, said mesh screen having an outer edge molded into said tubular body such that said outer edge extends circumferentially around an interior wall of said tubular body.

19. A kidney stone specimen collection device comprising:

a tubular body having a longitudinal axis, said tubular body having a diameter of no less than two inches;

a kidney stone removal means affixed to an interior of said tubular body and extending transverse to said longitudinal axis of said tubular body, said kidney stone removal means being a mesh screen, said kidney stone removal means for separating a kidney stone from a flow of urine passing through said tubular body, said mesh screen positioned generally centrally along said longitudinal axis within said tubular body;

a first closure means removably affixed to one end of said tubular body, said first closure means for selectively sealing said one end of said tubular body;

a second closure means removably affixed to an opposite end of said tubular body, said second closure means for selectively sealing said opposite end of said tubular body; and a flow indicator means positioned on an exterior surface of said tubular body, said flow indicator means for indicating a desired direction of urine flow through said tubular body.

\* \* \* \* \*